US 6,748,949 B2

(12) United States Patent
Smaldone

(10) Patent No.: US 6,748,949 B2
(45) Date of Patent: Jun. 15, 2004

(54) FACE MASKS FOR USE IN PRESSURIZED DRUG DELIVERY SYSTEMS

(76) Inventor: Gerald C. Smaldone, 47 Main St., Setauket, NY (US) 11733-2862

(*) Notice: Subject to any disclaimer, the term of this patent is extended or adjusted under 35 U.S.C. 154(b) by 0 days.

(21) Appl. No.: 10/150,760

(22) Filed: May 17, 2002

(65) Prior Publication Data

US 2002/0195107 A1 Dec. 26, 2002

Related U.S. Application Data

(60) Provisional application No. 60/292,128, filed on May 18, 2001.

(51) Int. Cl.[7] .............................................. A62B 18/02
(52) U.S. Cl. ........................... 128/203.29; 128/205.25; 128/206.21; 128/206.24; 128/206.28
(58) Field of Search ....................... 128/200.14, 200.24, 128/203.12, 205.25, 214.18, 200.29, 200.27, 201.24, 203.29, 206.12, 206.14, 206.15, 206.21–207.18

(56) References Cited

U.S. PATENT DOCUMENTS

| 4,865,027 A | * | 9/1989 | Laanen et al. | ......... 128/200.21 |
|---|---|---|---|---|
| 5,065,756 A | * | 11/1991 | Rapoport | ............... 128/204.18 |
| 5,400,781 A | | 3/1995 | Davenport | ............. 128/206.28 |
| 5,704,063 A | * | 1/1998 | Tilden | ............................... 2/9 |

FOREIGN PATENT DOCUMENTS

| DE | 37 18415 | 12/1988 |
|---|---|---|
| DE | 200 16 362 | 3/2001 |
| WO | 89/00874 | 2/1989 |

* cited by examiner

*Primary Examiner*—Glenn K. Dawson
(74) *Attorney, Agent, or Firm*—Darby & Darby

(57) ABSTRACT

Face masks for use in pressurized drug delivery applications, such as aerosol drug delivery systems, and a method of reducing aerosol deposition in the region of the eyes are presented. The face masks according to the various embodiments disclosed herein contain features that reduce the inertia of the aerosolized drug in perinasal areas. This results in a reduction in the amount of aerosolized drug that is deposited in the region of the eyes by inertial impaction, while at the same time, the features are constructed to maintain the flow of the aerosolized drug into the face mask so that the aerosolized drug is effectively delivered to the respiratory system of the patient.

26 Claims, 17 Drawing Sheets

Table 1

| Mask | No. of Experiements (n) | Mean Deposition as % Neb Charge | | | Eyes as % Face |
|---|---|---|---|---|---|
| | | Inhaled Mass | Face Including Eyes | Eyes Only | |
| Laerdal | 4 | 5.76 | 1.81 | 1.22 | 0.67 |
| M_Laerdal | 4 | 7.03 | 0.53 | 0.18 | 0.34 |
| Laerdal_ShortEyeCut | 2 | 7.15 | 0.57 | 0.18 | 0.32 |
| M_Laerdal_ShortEyeCut | 2 | 7.10 | 0.60 | 0.13 | 0.22 |
| Laerdal_LargeEyeCut | 4 | 7.87 | 0.69 | 0.10 | 0.14 |
| M_Laeral_LargeEyeCut | 4 | 8.11 | 0.60 | 0.10 | 0.16 |

Fig. 10

Table 2

| Mask | Nebulizer | No. of Experiements (n) | Mean Deposition as % Neb Charge | | | Eyes as % Face |
|---|---|---|---|---|---|---|
| | | | Inhaled Mass | Face Including Eyes | Eyes Only | |
| Laerdal | Pari LC Plus | 2 | 4.499 | 0.846 | 0.468 | 55.4% |
| M_Laerdal | Pari LC Plus | 2 | 8.66 | 0.63 | 0.18 | 28.5% |
| Laerdal_ShortEyeCut | Pari LC Plus | 2 | 8.85 | 0.97 | 0.33 | 33.7% |
| M_Laerdal_ShortEyeCut | Pari LC Plus | 2 | 6.92 | 0.54 | 0.13 | 23.5% |
| Laerdal_LargeEyeCut | Pari LC Plus | 2 | 8.09 | 0.75 | 0.18 | 23.7% |
| M_Laeral_LargeEyeCut | Pari LC Plus | 2 | 7.84 | 0.69 | 0.14 | 20.3% |

Fig. 15

FACE MASKS FOR USE IN PRESSURIZED DRUG DELIVERY SYSTEMS

CROSS REFERENCE TO RELATED APPLICATION

This application claims the benefit of U.S. patent application Ser. No. 60/292,128, filed May 18, 2001, which is hereby incorporated by reference in its entirety.

BACKGROUND OF THE INVENTION

1. Field of the Invention

The present invention relates to a mask and more particularly, to a face mask for use in delivering an aerosolized drug or the like to a patient.

2. Description of Related Art

Masks are commonly used in a wide range of applications and have widespread use in a number of medical settings. For example, masks are typically used in administering gases to a patient, e.g., an anesthetic agent, and more recently, masks have been increasingly used in drug delivery systems, including nebulizer drug delivery systems and metered dose inhalers using valved holding chambers (MDI/VHC). Nebulization is the application of a drug to a patient by means of an aerosol produced by a flow of gas. The aerosol and the drug are breathed in through the mask and are administered into the respiratory system of the patient as the patient inhales. The MDI/VHC creates its aerosol from the expansion of a volatile liquid into a gas within the VHC.

Nebulization is particularly used in the pediatric field as a means for delivering a drug or the like. In patients, such as young children, who have limited cooperation and attention span, the delivery of an aerosolized drug is carried out primarily with the use of a face mask. The face mask is placed over the nose and mouth of the patient, held in place by a caregiver or by using conventional straps or the like. The face mask is attached to an aerosol drug delivery device. In the case of nebulizers, the face mask is pressurized by the flow from the nebulizer and aerosol fills the mask becoming available for inhalation via the nose or the mouth. When the patient inhales, a negative pressure is applied to the face mask reservoir and the aerosolized drug is inhaled and enters into the respiratory system of the patient.

Metered dose inhalers are also used with face masks to disperse a drug to a patient. These devices dispense a predetermined amount of drug when activated and the patient is required to inhale in order to draw the aerosolized drug into the face mask reservoir and subsequently into the respiratory system of the patient.

Nebulizer drug delivery is different from drug delivery using a metered dose inhaler particularly in the degree of pressurization of the face mask. Metered dose inhalers can pressurize the mask to some degree, especially if aerosol is sprayed directly into the mask and a spacer is not used. A spacer is a device which is placed between the face mask and the source of aerosol (typically a bottle). Often, the spacer has one way valves and therefore is called a "valved holding chamber" (VHC). Face masks are used for both nebulizer drug delivery and for metered dose applications, but there are several associated shortcomings.

Nebulizers readily pressurize the mask and deliver more drug but leaks around the face are enhanced, resulting in increased facial deposition of the drug. Thus, leakage around the mask affects the performance of the particular device and in the case of nebulizers, leakage actually enhances the delivery of the drug; however, it is enhanced at the price of increased facial deposition and potentially local side effects. In order to effectively administer the aerosolized drug into the respiratory system of the patient, the face mask should cover the entire mouth and nasal openings of the patient.

The face mask is generally arranged so that it seats against the cheeks of the patient and extends across an upper portion of the bridge of the patient's nose. Because the bridge of the nose is elevated relative to the rest of the patient's face, e.g., cheeks, the upper portion of the face mask is slightly elevated relative to surrounding portions of the face mask which extend across the cheeks and under the mouth of the patient. This occurs even when the patient attempts to produce a tight seal between the mask and the face. For nebulizers, this produces certain leakage areas where the aerosolized drug can be discharged underneath the face mask and into the atmosphere. Because of the design of face masks and their above-described placement over the face, leakage is universally present in the perinasal areas on either side of the nose. This results in a jet of leaked aerosol being oriented and deposited directly into the eyes of the patient. In other words, aerosol is discharged underneath the face mask in these perinasal areas and flows directly towards the patient's eyes and unfortunately, many of the conventional masks are constructed in such a manner that the leaks that do occur are characterized as being high powered leaks (high kinetic energy) due to the high velocity that the fluid has as it flows underneath the mask and along the face directly into the eyes.

This may lead to several undesired side effects. For example, deposition of the leaked aerosolized drug may be associated with direct trauma to the eyes and associated structures. As leakage occurs, these organs are exposed to the aerosolized drug. There is speculation that the risk of developing cataracts increases as a result of aerosolized drugs being directly deposited in the eyes of the patient. At the very least, leakage of aerosolized drugs causes discomfort as the aerosol, traveling at a great velocity, is discharged underneath the face mask and deposits in the perinasal areas, including the eyes. In addition, leaks of certain aerosols can cause dermatological problems in some patients due to an adverse reaction between facial skin and the aerosol. Other undesirable conditions may result from having the aerosolized drug leaking and being deposited onto the face.

The disadvantages associated with conventional mask constructions are readily apparent by viewing FIGS. 1, 1*a* and 2. FIG. 1 is a front perspective view of a typical face mask 10 (that is commercially available from Laerdal Medical Corporation of Wappingers Falls, N.Y.). While, the face mask 10 is illustrated as being worn by an adult in FIGS. 1 and 1*a*, it will be understood that face mask 10 is designed to be worn by small children and finds particular application in pediatric care where the patient is unable or uncooperative in the administration of the drug. The face mask 10 has a body 12 including a peripheral edge 14 which is intended to engage a face of a patient. The body 12 defines a face mask reservoir in which the patient's nasal openings and mouth are in communication. The body 12 is typically made of a flexible material, such as a thermoplastic, e.g., a PVC material. The body 12 has a central opening 16 defined in part by an annular flange-like member 18 which extends outwardly from an outer surface 19 of the body 12. During use, the member 18 is coupled to other components of a drug delivery system (not shown) to permit delivery of the aerosolized drug. The opening 16 serves as a means for delivering the aerosolized drug to the patient. Depending upon the type of drug delivery assembly that is being used, e.g., a metered dose inhaler or a nebulizer system, the opening 16 receives the aerosolized drug as it is transported to the face mask reservoir defined by the body 12. The breathing action of the patient causes the aerosolized drug to be inhaled by the user and introduced into the patient's respiratory system.

As previously mentioned, one of the deficiencies of the face mask 10 is that leakage areas form around the peripheral edge 14. More specifically, the peripheral edge 14 does not form a complete seal with the face of the patient and accordingly, leakage flow paths 17 with high local velocities are formed at certain areas along the periphery of the face mask 10, especially in perinasal areas 15. In fact, maneuvers to reduce leaks along edge 10 may increase the velocity of leaks in perinasal areas 15. The perinasal areas 15 are particularly prone to the formation of leaks and this results in the aerosolized drug being discharged directly into the eyes and the associated structures. As previously mentioned, there are at least two different types of aerosolized drug delivery systems that are commonly used with a face mask, such as face mask 10. One type utilizes a pressurized metered dose inhaler (MDI/VHC) and the other type utilizes a jet nebulizer.

FIGS. 1 and 1a illustrate the face mask 10 as part of an aerosol drug delivery system that utilizes a jet nebulizer 20. The nebulizer 20 is operatively coupled to a compressor (not shown) which generates compressor air through the nebulizer 20. The nebulizer 20 has a body 30 which is coupled to a hose 31 that connects to the compressor at a first section 32 and is constructed so that compressor air flows therethrough. The drug to be delivered is stored in the body 30 using conventional techniques. A second section 34 of the nebulizer 20 communicates with the face mask reservoir so that the aerosolized drug is delivered into the face mask reservoir. The body 30 can include conventional venting and filtering mechanisms.

During aerosol generation, compressor air flows through the body 30 and into the face mask reservoir. This results in pressurization of the face mask 10 and also facilitates leaks at various locations (especially, the perinasal areas) around the face mask 10 with enhanced facial deposition being realized. Once the face mask 10 becomes fully pressurized, excess compressor air (including the aerosolized drug) is vented through an exhaust vent. This results in some of the aerosolized drug being lost into the surrounding environment. The face mask 10 is partially depressurized when the patient inhales but then as soon as the patient stops inhaling and exhales, the face mask 10 is again fully pressurized because of the continuous flow of the compressor air.

When the face mask is placed on a patient, an imperfect seal between the peripheral edge 14 of the face mask 10 and the patient's face typically results due to a number of factors (including face contour of the specific patient). This occurs for small children, children, and adults. The leaks that occur due to the pressurization of the face mask 10 result in the aerosolized drug flowing according to flow paths indicated by arrows 17. These leaks occur around the nose (perinasal areas), the cheeks and at the chin of the patient. It has also been found that the degree of pressure applied to the mask in an attempt to improve the seal between the face mask and the face does not necessarily improve and may in fact worsen the leakage of the aerosolized drug in the perinasal areas when the patient inhales and draws the aerosolized drug into the face mask reservoir. During therapy, local pressure on standard masks may facilitate high local velocities that can lead to eye deposition. For example a caregiver pressing on the mask can seal leaks along the cheeks but promote leaks around the eyes. The leakage of the aerosolized drug in the perinasal areas results in the aerosolized drug being discharged towards the eyes of the patient at high velocities due to the high kinetic energy of the fluid. This is less than ideal as it may cause discomfort at the very least and may also lead to other medical complications due to the drug being discharged into the eyes of the patient.

Eye deposition is thus particularly a problem for those drug delivery systems that exert greater pressure on the face mask and/or maintain the face mask reservoir under pressure. Because pressurization of the face mask 10 plays an important role in a nebulizer drug delivery system and nebulizers have become an increasingly popular means for delivering an aerosolized drug to a patient in such a manner that exhibits a high degree of pressurization in the face mask, the present applicant has studied the amount of eye deposition which occurs when face mask 10 is used in combination with the nebulizer 20 since the face mask pressurization associated with nebulizer use promotes a higher level of leakage around the eye region.

FIG. 2 is a gamma camera image obtained using a simulator face as part of a radiolabel face deposition study carried out using the face mask 10 of FIG. 1 in combination with the nebulizer 20. In these studies, the face mask 10 was attached to a breathing emulator (not shown) which simulated the breathing pattern of a particular type of patient. The breathing emulator includes a three dimensional, contoured bench model face to which the face mask 10 was attached. A filter was placed in the mouth of the bench model face so as to best determine the inhaled mass (actual quantity of aerosol inhaled) as the filter represents the final path of the particles passing into patient.

By using nebulized radiolabeled saline acting as a surrogate drug in the nebulizer 20, the deposition pattern of the particles can easily by determined. FIG. 2 represents deposition following tidal breathing (also referred to as tidal volume) of 50 ml with a minute ventilation of 1.25 liters/min, a pattern typical of a small child. Airflow from the nebulizer 20 is 4.7 liters/minute and therefore the face mask 10 is highly pressurized. Under these conditions, aerosolized drug leaks from the mask at various points on the face, as evidenced by the concentrated areas appearing in the image. As seen in FIG. 2, there is a high level of deposition in the area of the eyes of the patient and there is also a high level of deposition in the chin and jaw areas of the patient. It will be appreciated that other aerosol drug delivery systems which cause the face mask to become pressurized will likely generate similar data showing eye deposition of the aerosolized drug.

While face masks having been developed with venting mechanisms to cope with the pressurization requirements of a nebulizer or the like, these face masks still suffer from the disadvantage that they have constructions that not only permit aerosolized drug to be discharged in the perinasal areas but more importantly, the aerosolized drug is discharged at high velocities toward the eyes due to the imperfect interface between the face mask and the face. In effect, this imperfect interface "funnels" the aerosolized drug so that the aerosolized drug exits the face mask at a high velocity toward the eyes.

What is needed in the art and has heretofore not been available is a face mask which reduces the inertia of the aerosolized drug in the perinasal areas thus reducing deposition in the region of the eyes by inertial impaction, while maintaining flow of the aerosol into the face mask so that the aerosolized drug is effectively delivered to the respiratory system of the patient. The exemplary face masks disclosed herein satisfy these and other needs.

SUMMARY OF THE INVENTION

In one exemplary embodiment, a face mask for use in pressurized drug delivery applications, such as aerosol drug delivery systems, and a method of reducing aerosol deposition in the region of the eyes are presented. The face masks according to the various embodiments disclosed herein contain features that reduce the inertia of the aerosolized drug in perinasal areas. This results in a reduction in the amount of aerosolized drug that is deposited in the region of the eyes by inertial impaction, while at the same time, the features are constructed to maintain the flow of the aerosolized drug into the face mask so that the aerosolized drug is effectively delivered to the respiratory system of the patient.

According to one exemplary embodiment, the face mask has a body having a peripheral edge for placement against a face of a patient. A nose bridge section is formed in an upper section of the mask body to seat against the nose of the patient when the mask is placed against the face during the application. The body has a pair of eye vents formed therein, with one eye vent being formed on one side of the nose bridge section and the other eye vent being formed the other side of the nose bridge section. When the face mask is worn by the patient, the eye vents are generally orientated underneath the eyes of the patient. The eye vents are thus eye cut outs formed along the peripheral edge of the mask body by removing mask material. The present applicant has found that opening the face mask at the sites of the greatest risk (i.e., the eyes), where aerosolized drug flow is not desired, compels and ensures the local reduction of particle inertia at the sites most at risk of facial damage and irritation. The excisions in the face mask that serve as eye vents thus minimize the local velocity and particle inertia such that the particles do not impact on the surface of the face and eyes and actually pass over the face and eyes without deposition thereon. This results in a substantial reduction of deposition in the region of the eyes compared to conventional face masks.

The eye cut outs can be formed in any number of different sizes and any number of different shapes (e.g., semicircular) based upon the performance characteristics (i.e., inhaled mass value, facial deposition amount, etc.) that are desired in the application of the aerosolized drug. The eye vents can also be used in combination with a supplemental vent that is also formed in the face mask body. For example, the supplemental vent can be in the form of an opening that is formed in the mask in a lower chin section near the peripheral edge. By providing eye vents in the face mask, a face mask is provided that substantially alleviates or eliminates the discomfort and potential harmful consequences that are associated with face masks that have leaks in the perinasal areas which result in the aerosolized drug being "funneled" between the peripheral edge of the face mask and the face and causing the aerosolized drug to flow at great velocities into the eyes of the patient.

Further aspects and features of the present invention can be appreciated from the appended Figures and the accompanying written description.

BRIEF DESCRIPTION OF THE DRAWINGS

FIG. 10 is a table illustrating the mean deposition (of inhaled mass, face including eyes, and the eyes only) as a percent of the nebulizer charge when the conventional face mask of FIG. 1 and the face masks according to the present exemplary embodiments are used;

FIG. 15 is a table illustrating the mean deposition (of inhaled mass, face including eyes, and the eyes only) as a percent of the nebulizer charge when the face masks according to the present exemplary embodiments are used.

DESCRIPTION OF A PREFERRED EMBODIMENT

Figure 3:
FIG. 3 is a front perspective view of a face mask according to a first exemplary embodiment shown as part of a nebulizer drug delivery system and in a typical administering position on a patient such that it is arranged so that the mask covers the nose and mouth of the patient, wherein a portion of the face mask is cut away to illustrate a vent formed therein.

FIG. 3 is a front perspective view of an exemplary face mask 100 according to a first embodiment. For purposes of illustrating the benefits of the present invention, the face mask 100 is of a similar construction as the face mask 10 with one exception, as explained below. The face mask 100 thus includes a body 102 including a peripheral edge 104 which is intended to engage a face of a patient. The body 102 defines a face mask reservoir in which the patient's nasal openings and mouth are in communication. The body 102 is typically made of a flexible material, such as a thermoplastic, e.g., PVC material. The thickness of the material and cross-section varies to allow different parts of the exemplary face mask 100 to carry out their normal function. Thus, for example, the face mask 100 is generally of a relatively thin material with the peripheral sealing edge 104 also being of a thin flexible construction so that it can flexibly engage the face of the patient. The body 102 has a central opening 106 defined in part by an annular flange-like member 108 which extends outwardly from an outer surface 109 of the body 102.

The exemplary face mask 100 has a vent 110 formed in the face mask 100 for decompressing the face mask 100 and also for modifying the flow of the aerosolized drug that flows underneath the face mask 100 (especially in the perinasal areas) during a normal application when the face mask 10 is placed against the face. The exemplary vent 110 is a generally circular shaped opening; however, the shape of the vent 110 is not critical. The vent 110 is formed in the face mask body 102 at the 6 o'clock position. In other words, the vent 110 is generally formed in the chin area of the face mask 100. The peripheral edge 104 extends completely around the face mask 100 and therefore the vent 110 is formed slightly away from the patient's face. This is desirable as the vent 110 serves to discharge aerosol and therefore, it is preferred to direct the aerosol downward and away from the patient's face. The effect of forming the vent 110 is discussed in greater detail hereinafter during the discussion of the data presented in FIGS. 9 and 10. The dimensions of the vent 110 can be varied depending upon a number of factors, including the precise application, the size of the face mask, etc., so long as the vent 110 has sufficient dimensions that permit a desired amount of the aerosolized drug to be inhaled by the patient, while at the same time, the face and eye deposition is reduced. For example and according to one exemplary embodiment, the face mask 100 has an inner surface area of about 110 cm$^2$ and the vent 110 is formed so that the opening defined thereby has an area of approximately 3.1 cm$^2$. It will be appreciated that the vent 110 can be formed such that its dimensions are different than the above example as the above example is merely illustrative and not limiting. For example, the vent 110 can be formed to occupy an area from about 2.0 cm$^2$ to about 6.0 cm$^2$ in another embodiment.

While the vent 110 does serve to reduce aerosol deposition in the facial areas and also serves to decompress the face mask 100, the Applicant realized that (1) even those face mask with vents still have leaks between the face mask and the face (especially the perinasal areas thereof) which permits aerosolized drug to vent and (2) to increase the safety of face masks, it is more desirable to control the flow characteristics of the aerosolized drug that is discharged in the perinasal areas. Based on this information, the Applicant constructed a face mask that reduces face and eye deposition by modifying the flow characteristics of the aerosolized drug in the perinasal areas.

Figure 4:
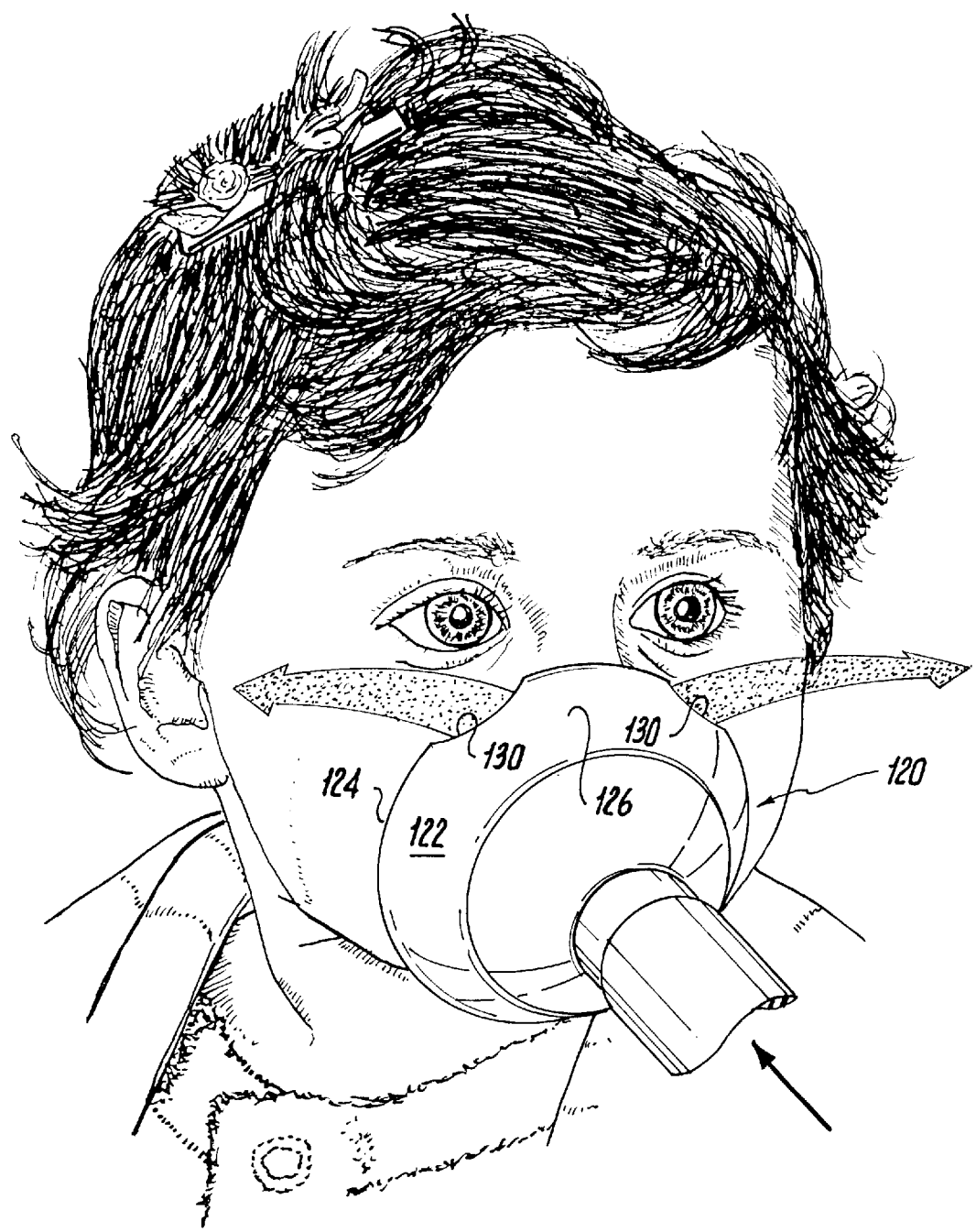
FIG. 4 is a front perspective view of a face mask according to a second exemplary embodiment shown as part of a nebulizer drug delivery system and in a typical administering position on a patient such that it is arranged so that the mask covers the nose and mouth of the patient, wherein the face mask has a pair of eye vents formed therein.

Referring now to FIG. 4, an exemplary face mask 120 according to a second embodiment is illustrated. The exemplary face mask 120 has a body 122 similar to the body 12 of the face mask 10 of FIG. 1 with the exception that the face mask 120 has a pair of eye cut-outs or vents 130 formed by removing mask material along a peripheral edge 124 of the body 122. The eye vents 130 are formed on each side of a bridge section 126 of the face mask 120. The bridge section 126 is the mask section that generally seats against the bridge of the nose and interfaces with the cheeks of the patient adjacent the nose. The illustrated eye vents 130 are formed at the peripheral edge 124 and extend inwardly therefrom so as to remove mask material along the peripheral edge 124 under the patient's eyes. Each of the illustrated eye vents 130 has a semicircular shape; however, the precise shape of the eye vents 130 is not critical. For example, the eye vents 130 can alternatively be formed to have more of a rectangular shape in comparison to the semicircular or angular eye vents 130 shown in FIG. 4.

The eye vents 130 vent aerosolized drug flow from the mask into the region of the eyes. Contrary to one's initial inclination of not providing vents directly in the area where aerosolized drug flow is not desired, the Applicant has discovered that the provision of eye vents 130 in the eye region actually greatly improves the performance and the safety of the face mask 120 by altering the flow characteristics of the aerosolized drug in the eye region (i.e., the perinasal areas). One way of understanding the advantages provided by the eye vents 130 is by investigating the particle inertia of the fluid in the area of interest, namely the region of the eyes. In general, the deposition of particles is related to the diameters of the particles (hereinafter "a"), the velocity of the particle movement imparted by the local flow through the leak (hereinafter "U") in the face mask, and the local geometry between the face mask and the face (hereinafter "D"). All of these factors can be described together via local Stokes numbers (hereinafter "Stk"). Stk is dimensionless term that is related to particle inertia. The greater the inertia of particles, the greater the tendency for these particles to impact the face (eyes) and deposit on the face. Equation (1) sets forth the general relationship between the various variables:

$$Stk \alpha [a^2(U)]/D \qquad \text{(Equation 1)}$$

where D can be related to U as set forth in Equation (2):

$$U \alpha Q/D \quad \text{(Equation 2)}$$

where Q is the volume rate of flow out of the area of the mask that exhibits leakage. It will be appreciated that increases in local diameter of the site of the leak, decreases local linear velocity. That is, the particle inertia is affected by the diameter of the particles (a), the local velocity of the fluid (U) and has an inversion relationship relative to the local diameters (D).

The exemplary face mask 120 reduces Stk by increasing D which results in a decrease in U (Equation 2) and Stk. Further effects on U occur via mask decompression as reducing pressure within the mask further reduces Q. The latter accomplished via the opening D, which acts as a vent.

The face mask 120 provides a face mask where aerosol flow into the face mask is maintained (which is necessary for effective drug delivery), while at the same time, the construction of the face mask 120 reduces the deposition of aerosol in the region of the eyes and the rest of the face by opening the face mask 120 in the region of the eyes. Opening the face mask 120 at the sites of the greatest risk and at the very locations where aerosolized drug flow is not desired (the eyes) compels and ensures the local reduction of particle inertia at the sites most at risk of facial damage and irritation. Advantageously, the provision of eye vents 130 reduces particle velocity by increasing the space between the mask (increased Stokes Diameter (D)) and further, by decompressing the face mask reservoir (the area between the face and the inner surface of the face mask 120 when it is worn), the pressure within the face mask reservoir is reduced and this minimizes linear flow to the eyes (i.e., variable (U) of Equation 2). It will be understood that the local Stokes numbers are merely a tool to describe the advantages of the present face masks and in no way limit the scope of the present face masks as the principle can be understood by other means.

The wide excisions in the face mask 120 that serve as the eye vents 130 minimize the local velocity and particle inertia such that the particles (i.e., the aerosolized drug) do not impact on the surface of the face and eyes and actually pass over the face and eyes without deposition thereon. Accordingly, the eye vents 130 are formed generally underneath the eyes (while leaving the bridge section of the face mask in tact) in order to obviate the high pressure effects that were previously observed at the peripheral edge 124 of the face mask 120 due to the aerosolized drug escaping in this region at high velocities. By forming eye vents 130 by removing sections of the face mask 120, including peripheral edge portions thereof, the interface between the peripheral edge 124 and the face is eliminated in this region and therefore, aerosolized drug is no longer "funneled" out of the mask 120 at the perinasal areas at great velocities. Thus, low velocities in this region are ensured independent of other multiple uncontrollable variables (pressure of the mask on the face, nebulizer flow into the mask) and deposition is always minimized.

Thus, the face mask 120 enhances the safety performance of the face mask by reducing the velocity of the aerosolized drug as it vents from the face mask 120 due to the face mask/face interface being obviated in the eye region. In this embodiment, the eye vents 130 are of reduced dimensions compared to other embodiments. For example, the face mask 120 has an inner surface area of about 110 cm$^2$ and the eye vents 130 are formed so that they occupy an area of about 5.5 cm$^2$. However, these dimensions are merely exemplary and it has been found that the eye vents 130 can have a variety of dimensions since the present advantages are derived more from the provision of the eye vents themselves in the face mask and the location of the eye vents 130 in comparison to specific dimensions of the eye vents 130.

Figure 5:
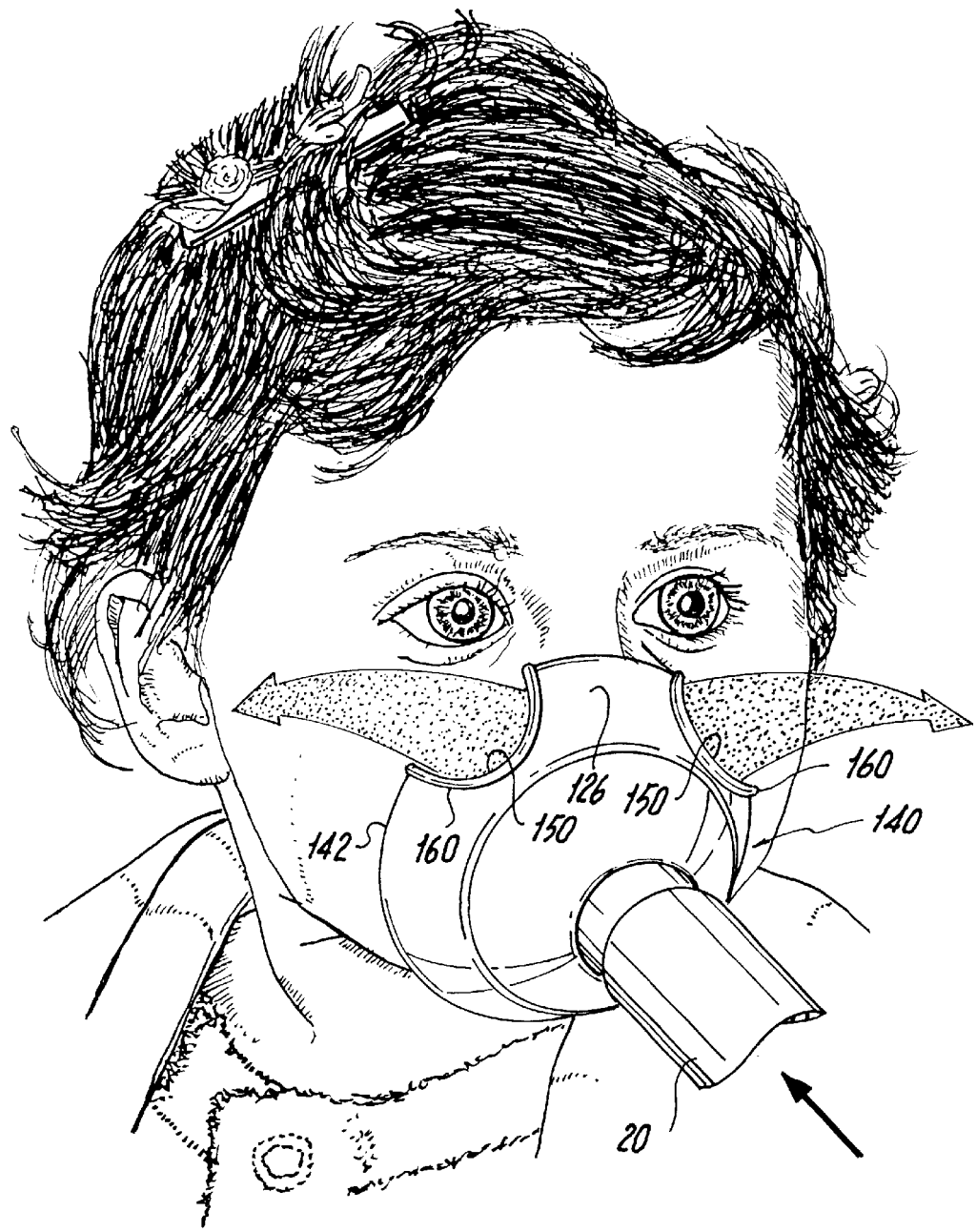
FIG. 5. is a front perspective view of a face mask according to a third exemplary embodiment shown as part of a nebulizer drug delivery system and in a typical administering position on a patient such that it is arranged so that the mask covers the nose and mouth of the patient, wherein the face mask has a pair of reinforced eye vents formed therein.

FIG. 5 shows a face mask 140 according to a third embodiment. The face mask 140 is very similar to the face mask 120 of FIG. 4 with the exception that the eye vents 150 have been enlarged in comparison to the eye vents 130 of FIG. 4. For example, the face mask 140 has an inner surface area of about 110 cm$^2$ and the eye vents 150 occupy an area of about 10 cm$^2$; however, these dimensions are merely exemplary and not limiting since the eye vents 150 can occupy an area less than 10 cm$^2$ as well as an area greater than 10 cm$^2$. Once again, the eye vents 150 are formed in the region of the eyes and the eye vents 150 can be formed in any number of different shapes. The shapes of the eye vents 150 in FIG. 5 are merely exemplary in nature. In this particular embodiment using this particular type of face mask, the eye vents can occupy From about 5 cm$^2$ to about 11 cm$^2$; however, these dimensions can be varied outside of this exemplary range. For this exemplary range, the eye vents occupy from about 4.5% to about 10% of the total surface area of the face mask.

Since the excision of more and more mask material to form the eye vents 150 can serve to weaken the overall structural rigidity of the face mask 140, the eye vents 150 can be formed such that they each have a reinforcing member 160, which serves to reinforce the structural rigidity of the face mask 140 and ensure the robustness of the face mask 140. The reinforcing member 160 is thus preferably formed around a peripheral edge 142 that defines the eye vents 150 so as to increase the structural rigidity in the region of the eye vents 150. This ensures that the eye vents 150 substantially maintain their shape and form when the face mask 140 is placed on the patient's head and pressure is applied to produce some type of seal between the face mask 140 and the face.

The reinforcing member 160 can be any number of structures that either can be integral to the face mask 140 itself or can be later attached and secured to the face mask 140 after it has been fabricated and the eye vents 150 have been formed. For example, the reinforcing member 160 can be in the form of a reinforced rigid, plastic piece that is securely attached to the face mask 140 using conventional techniques, such as using an adhesive, bonding, etc. By incorporating a rigid element into the face mask construction, the region of the face mask 140 that includes the eye vents 150 is less likely to deform or collapse but rather remains well defined during use of the face mask 140. The reinforcing member 160 can also be in the form of a metal bushing that is attached to the face mask 140 using conventional techniques, such as those disclosed above. Further, the reinforcing member 160 can be integrally formed with the rest of the face mask 140 when the face mask 140 is fabricated. For example, the reinforcing member 160 for each eye vent 150 can be introduced into a mold and then the face mask 140 is formed therearound such that the reinforcing members 160 are integral with the face mask 140. It will also be appreciated that if the face mask 140 is formed using a molding process, two or more different materials can be used to form the reinforced face mask 140 in that one material can be used to form the reinforced members 160 and another material can be used to form the rest of the face mask 140.

Figure 6:
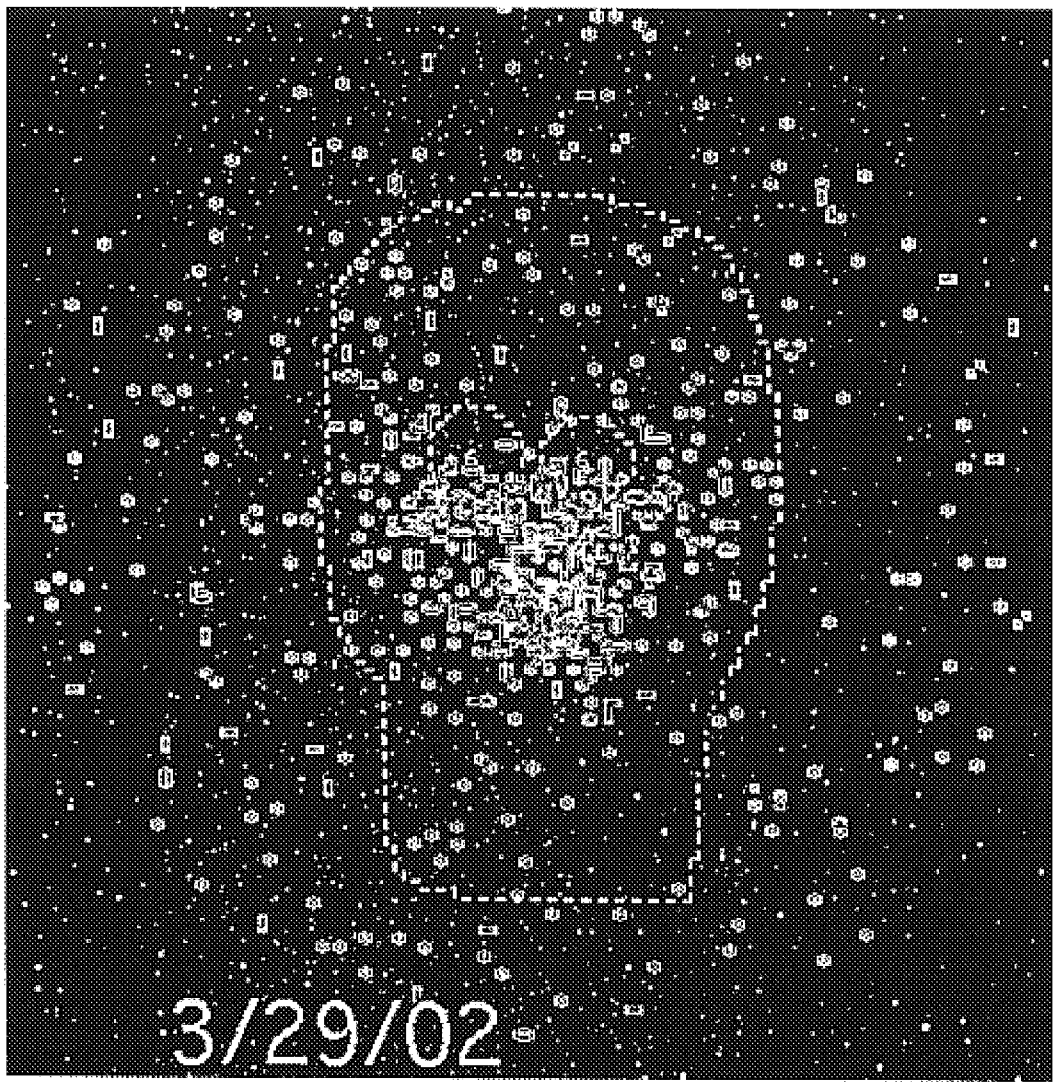
FIG. 6 is a an image obtained using a gamma camera scan of the face model as part of a radiolabel face deposition study carried out using the conventional face mask of FIG. 5 illustrating particle deposition (aerosol drug) occurring in response to a pediatric pattern of breathing (tidal volume 50 ml, frequency of breathing 25 breaths per min, duty cycle 0.4)

FIG. 6 is a gamma camera image obtained using a stimulator face as part of a radiolabel face deposition study carried out using a face mask 140 of FIG. 5. As with the other studies, the face mask 140 was attached to a breathing emulator (not shown) that simulates the breathing pattern of a particular type of patient. The visualized area represents the facial area and the eyes of the patient. By using nebulized radiolabeled saline acting as a surrogate drug in the nebulizer 20, the deposition pattern of the particles can easily be determined. FIG. 6 represents deposition following tidal breathing (tidal volume) of 50 ml with a minute ventilation of 1.25 liters/min. This is representative of a breathing pattern of a typical child. Airflow from the nebulizer 20 is 4.7 liters/minute and therefore, the face mask 140 is highly pressurized. Aerosolized drug leaks from the mask at various points on the face are evidenced by the concentrated areas appearing in the image. The visualized area represents the facial area and the eyes of the patient. In the study that yielded the results set forth in FIGS. 9 and 10, the nebulizer 20 was a nebulizer commercially available from PARI GmbH under the trade name Pari LC Plus.

Figure 1:
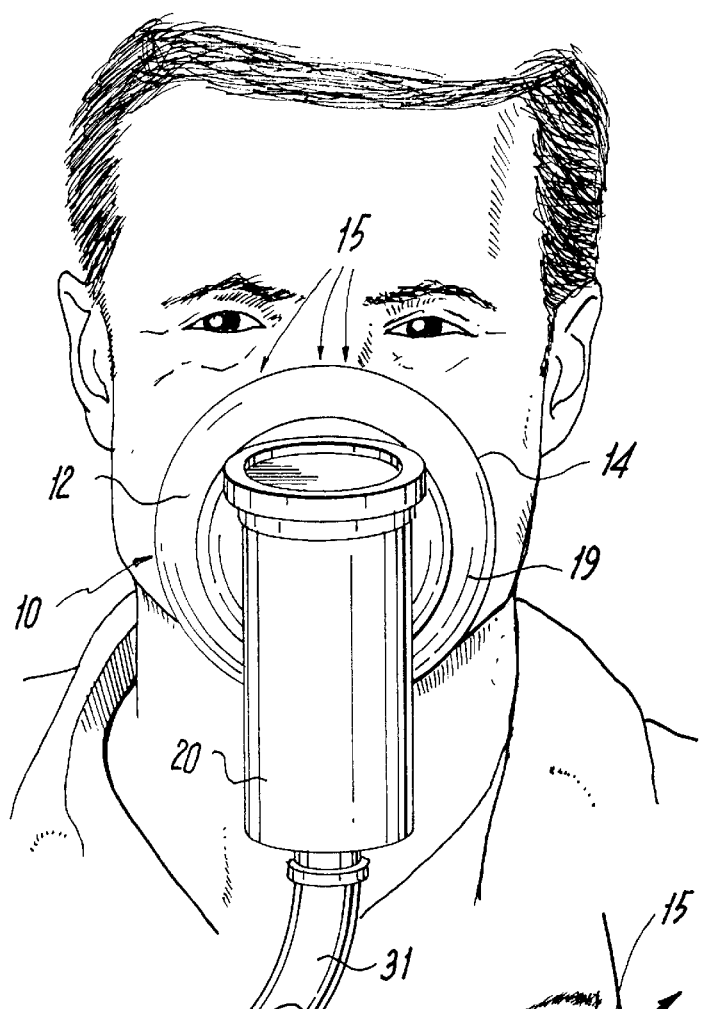
FIG. 1 is a front elevational view of a conventional face mask shown as part of a nebulizer drug delivery system and in a typical administering position on a patient such that it is arranged so that the mask covers the nose and mouth of the patient.
Figure 1A:
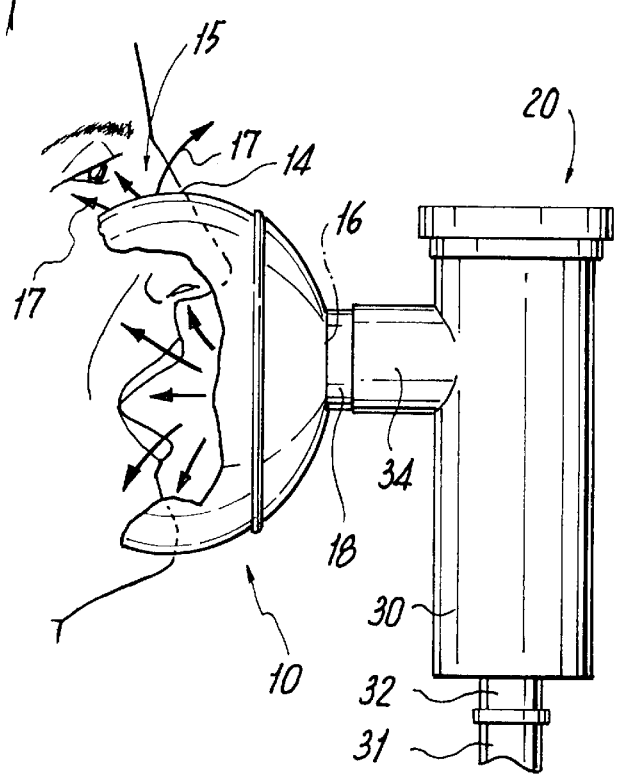
FIG. 1a is a side elevational view of the face mask of FIG. 1 with a section being cut-away to illustrate the flow paths of the aerosolized drug when the face mask is worn by a patient.
Figure 2:
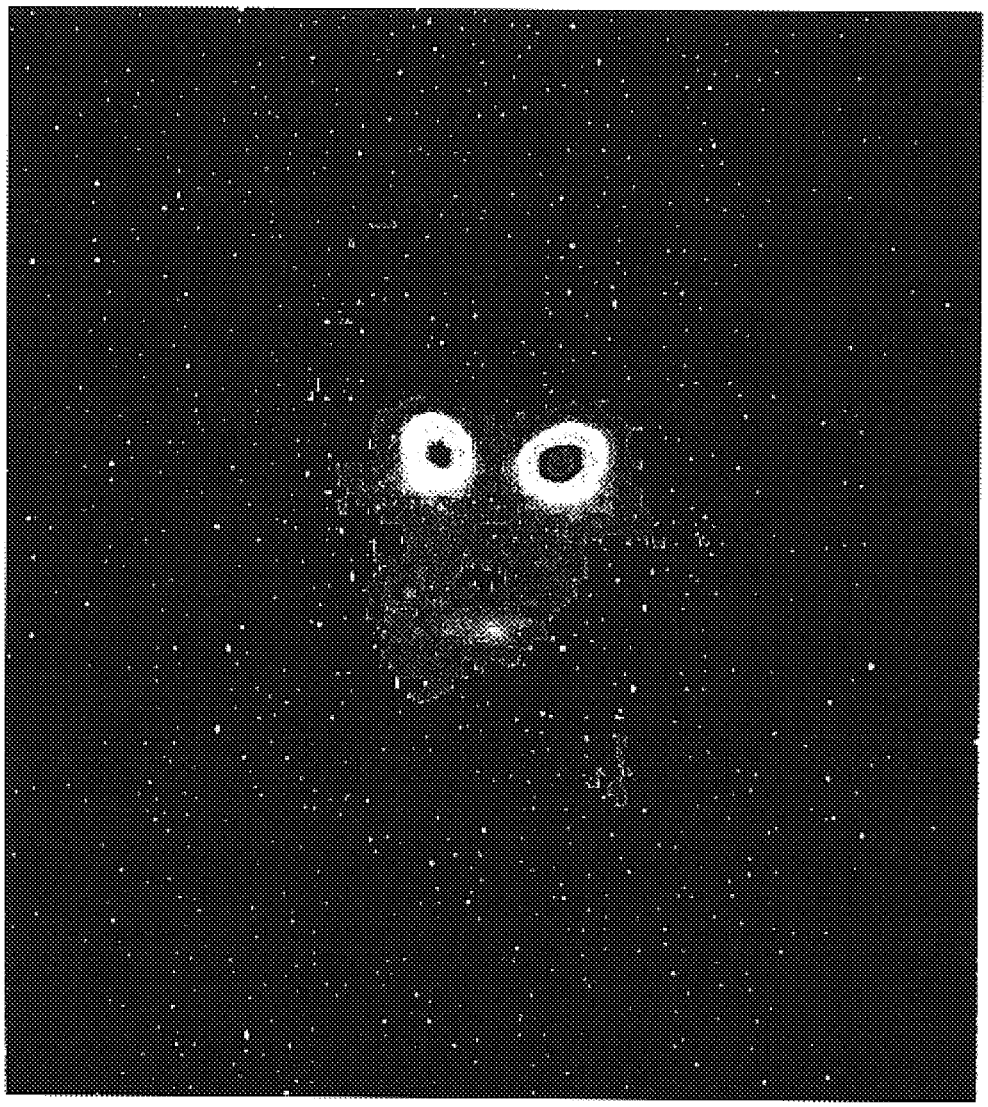
FIG. 2 is an image obtained using a gamma camera scan of a face model as part of a radiolabel face deposition study carried out using the conventional face mask of FIG. 1 illustrating particle deposition (aerosol drug) occurring in response to a pediatric pattern of breathing (tidal volume 50 ml, frequency of breathing 25 breaths per min, duty cycle 0.4)
Figure 9A:
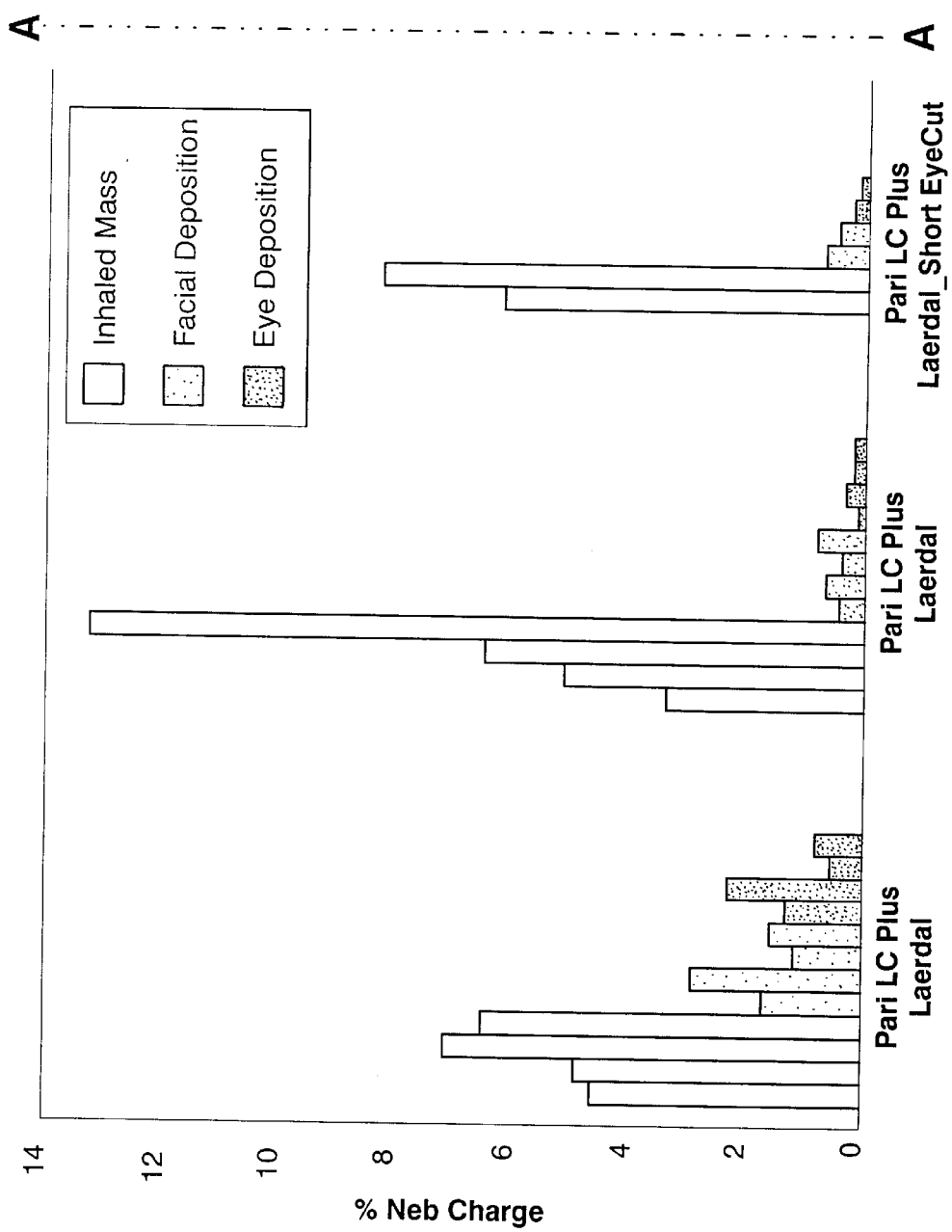
FIG. 9 is a schematic diagram in the form of a bar graph comparing drug delivery and facial deposition data obtained from testing the conventional face mask of FIG. 1 and a set of the exemplary face masks disclosed herein.
Figure 9B:
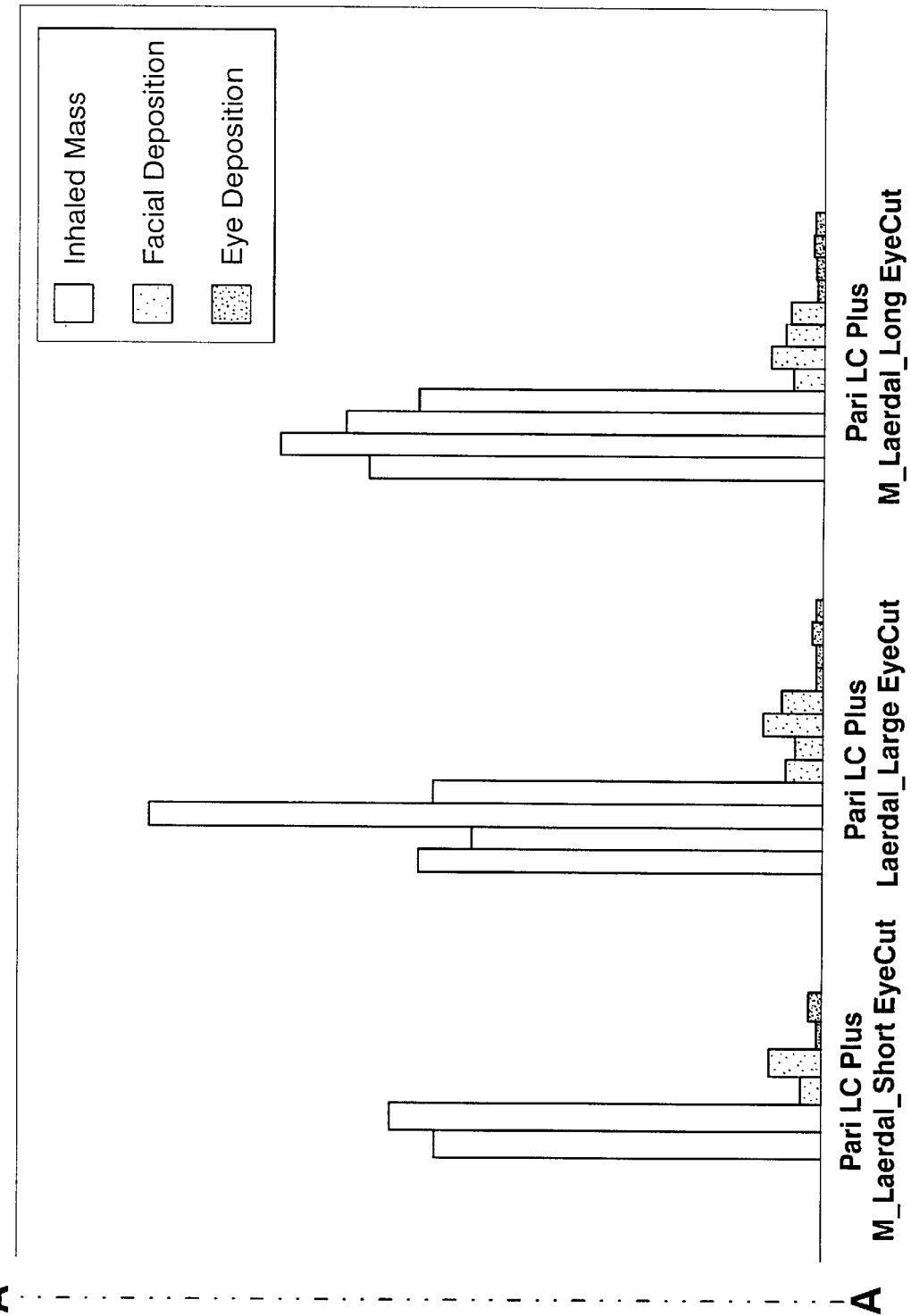

As seen in FIG. 6, the amount of facial deposition is dramatically reduced compared to the image of FIG. 2, which represents the facial deposition pattern of the same basic face mask without eye vents 150. In other words, the aerosol deposition is markedly reduced in the region of the eyes as well as the rest of the face. The bar graph of FIG. 9 and Table 1 of FIG. 10 summarize the quantitative measurements of deposition on the face, in the eyes and the drug delivery to the patient (inhaled mass). In FIGS. 9 and 10, the conventional face mask 10 of FIG. 1 is identified as "Laerdal", the face mask 100 of FIG. 3 is identified as "M Laerdal", the face mask 120 of FIG. 4 is identified as "Laerdal ShortEyeCut", and the face mask 140 of FIG. 5 is identified as "Laerdal LargeEyeCut".

As the data of FIGS. 9 and 10 reflects, using the conventional face mask 10 of FIG. 1 with nebulizer 20 resulted in 1.22% of the aerosolized drug initially placed in the nebulizer 20 being deposited in the region of the eyes of the patient (1.81% of the aerosolized drug was deposited on the face). Thus, the amount of the aerosolized drug that was deposited in the eyes as a percentage of the amount deposited on the total face was 67%. In other words, about ⅔ of the aerosolized drug that was deposited on the face was deposited in the area of highest risk, namely the eye regions. The inhaled mass (quantity of drug actually delivered to the patient) for the face mask 10 was 5.76% of the amount placed in the nebulizer 20.

When the face mask 100 of FIG. 3 was used, the inhaled mass increased to 7.03%, while at the same time, the amount of aerosolized drug being deposited in the region of the eyes decreased substantially to 0.18% (0.53% deposited on the face). Thus, only about ⅓ of the aerosolized drug that was deposited on the face was deposited in the region of the eyes. However, this data merely quantifies the results and does not characterize the flow properties of the aerosolized drug that does escape underneath the face mask and flows toward the eyes. In other words and as previously mentioned, the safety benefits accorded by the face mask are improved if not only less aerosolized drug is deposited in the region of the eyes (and on the face for that matter) but also if the flow characteristics of the escaping aerosolized drug are modified in the region of the eyes. The provision of eye vents in the face mask accomplishes these goals and enhances the overall safety of the face mask.

When the face mask 130 of FIG. 4 was used, the inhaled mass increased to 7.15%, while at the same time, the amount of aerosolized drug being deposited in the region of the eyes decreased substantially to 0.18% (0.57% deposited on the face). Thus, only about ⅓ of the aerosolized drug that was deposited on the face was deposited in the region of the eyes. When the face mask 140 of FIG. 5 was used, the amount of aerosolized drug that was deposited in the region of the eyes was about 0.10% with about 0.69% being deposited on the face. Thus, only about 14% of the aerosolized drug that was deposited on the face was deposited in the region of the eyes. This is a substantial improvement over the face mask 10 of FIG. 1, in which about 67% of the aerosolized drug that was deposited on the face was deposited in the region of the eyes. More specifically, the modification of the face mask 140 by forming eye vents 150 reduced eye deposition 92%. At the same time, use of the face mask 140 resulted in 7.87% of the aerosolized drug being inhaled (i.e., inhaled mass).

It will be appreciated that the provision of eye vents (of varying dimensions) in the face mask not only maintains an acceptable inhaled mass (and in most cases, results in an increase in the inhaled mass) but more importantly, the eye vents serve to modify the flow characteristics of the aerosolized drug (i.e., reduce the particle inertia of the aerosolized drug) in such a manner that results in increased safety since the high local velocities of the escaping aerosolized drug in the region of the eyes that plagued conventional face mask constructions is eliminated. In other words, the kinetic energy of the aerosolized drug in the region of the eyes is reduced by controlling the velocity of the aerosolized drug in the region of the eyes.

In the pediatric population, an inhaled mass value of about 4% is considered efficient for a drug delivery system. The low percentages are inherent to drug delivery systems in pediatrics because a large amount of the drug is wasted due to the drug either being vented from the mask as well as being trapped in the nebulizer or the like. The quantities deposited on the face and the eyes are low on a percentage basis but quite high on a drug delivery basis and thus it will be appreciated that facial and eye deposition in such pressurized drug delivery systems is a matter that deserves attention as it can lead to patient discomfort and can potentially lead to more serious complications, especially with the eyes.

According to one embodiment, the face mask includes eye vents that occupy greater than 10% of a total surface area of the face mask body. According to another embodiment, the face mask includes eye vents that occupy less than 10% of a total surface area of the face mask body. According to yet another embodiment, the face mask includes eye vents that occupy between about 2% and about 10% of a total surface area of the face mask body. The eye vents can also be formed to have dimensions such that an inhaled mass of an aerosolized drug supplied through the face mask is greater than 4% of an initial amount of aerosolized drug that is present in the drug delivery system and an amount of the aerosolized drug that is deposited in a region of the eyes is less than 24% of an amount of the aerosolized drug that is deposited on the face under a pattern of breathing that is characterized as having a tidal volume of 50 ml, a frequency of breathing of 25 breaths per minute and a duty cycle of 0.4.

Figure 7:
FIG. 7 is a front perspective view of a face mask according to a fifth exemplary embodiment shown as part of a nebulizer drug delivery system and in a typical administering position on a patient such that it is arranged so that the mask covers the nose and mouth of the patient, wherein the face mask has a pair of eye vents formed therein and wherein a portion of the face mask is cut away to illustrate a vent formed therein.

Now referring to FIG. 7 in which a face mask 170 is illustrated according to a fourth embodiment. Face mask 170 is a combination of the face mask 100 of FIG. 3 and the face mask 140 of FIG. 5 in that the face mask 170 includes not only the vent 110 but also includes the eye vents 150. It will be appreciated that while the exemplary vent 110 is located generally in the 6 o'clock position, the location of the vent 110 is not limited to this precise location and further, more than one vent can be formed in the face mask 170 and used in combination with the pair of eye vents 150. For example, a pair of vents (not shown) can be formed in the lower cheek areas of the face mask 170, with one vent being formed on one cheek and the other vent being formed on the other cheek.

Figure 8:
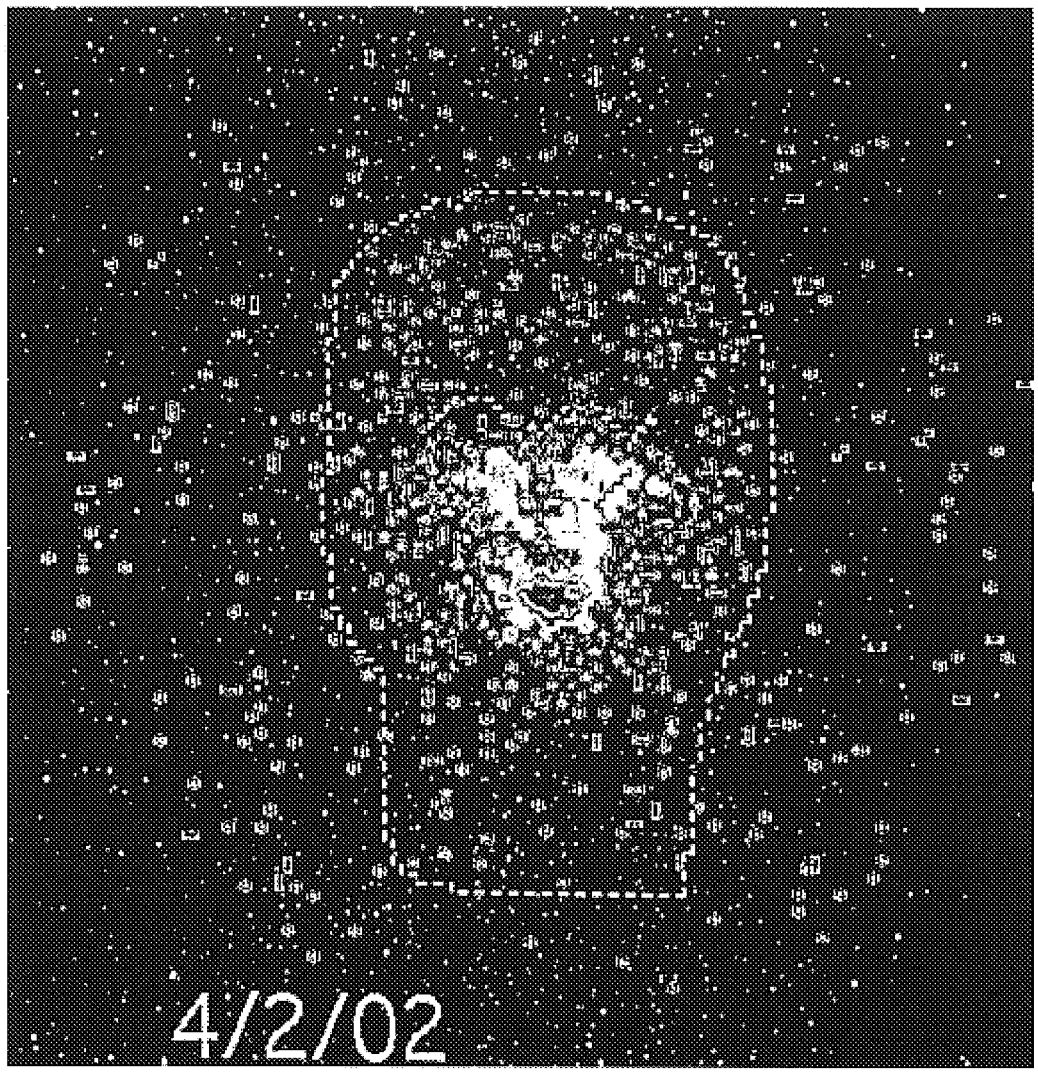
FIG. 8 is a an image obtained using a gamma camera scan of the face model as part of a radiolabel face deposition study carried out using the conventional face mask of FIG. 7 illustrating particle deposition (aerosol drug) occurring in response to a pediatric pattern of breathing (tidal volume 50 ml, frequency of breathing 25 breaths per min, duty cycle 0.4)

FIG. 8 is a gamma camera image obtained using a simulator face as part of a radiolabel face deposition study carried out using the face mask 170 of FIG. 7 in combination with the nebulizer 20. As seen in FIG. 8, the provision of vent 110 and eye vents 150 in combination results in a reduction of aerosolized drug deposition in the region of the eyes (as well as the face). The data contained in FIGS. 9 and 10 illustrate the benefits obtained by incorporating vent 110 and eye vents 150 into the face mask 170. More specifically, using the face mask 170 with the nebulizer 20, resulted in 0.10% of the aerosolized drug being deposited in the region of the eyes of the patient (0.60% on the face). At the same time, the inhaled mass increased to 8.11%. Thus, one will appreciate that while the vent 110 alone serves to reduce the amount of facial and eye deposition, the provision of eye vents 150 enhances the safety of the face mask 170 by locally modifying the flow characteristics (i.e., kinetic energy/local velocity) of the aerosolized drug in the region of the eyes. This is a marked improvement over the conventional face mask constructions that suffered from having perinasal areas that permitted jets of high velocity aerosolized drug to vent from underneath the face mask and be directed into the eyes.

Figure 11:
FIG. 11 is a front perspective view of a face mask according to a sixth exemplary embodiment shown as part of a nebulizer drug delivery system and in a typical administering position on a patient such that it is arranged so that the mask covers the nose and mouth of the patient, wherein the face mask has a pair of eye vents formed therein and wherein a portion of the face mask is cut away to illustrate a vent formed therein.

FIG. 11 illustrates a face mask 200 according to a fifth embodiment. The face mask 200 is of a different type of construction than the face mask 10 of FIG. 1; however, it is intended for use in drug delivery systems, such as those which employ a nebulizer. A face mask identical to or similar to the face mask 200 is commercially available from Ferraris Medical Inc. of Holland, N.Y. under the trade name Panda face masks. The face mask 200 has a body 202 that includes a peripheral edge 204 which is intended to engage a face of the patient. The body 202 is typically made of a flexible material, such as a thermoplastic, e.g., PVC material. The body 202 defines a face mask reservoir in which the patient's nasal openings and mouth are in communication. The body 202 has a central opening 206 defined in part by an annular flange-like member 208 which extends outwardly from an outer surface 209 of the body 202. As with the earlier face mask constructions, the member 208 is coupled with a component (e.g., nebulizer 20) of the drug delivery system to permit delivery of the aerosolized drug. The face mask 200 also preferably includes a vent for releasing excessive pressure build-up and also can include one or more other ports that receive one or more components of the drug delivery system. For example, some types of nebulizers or the like are intended to be connected to the face mask 170 at one or more of these ports instead of at the main flange-like member 118. The face mask 200 contains a bridge section 210 that is contoured to fit around the patient's nose.

In this embodiment, the face mask 200 includes a vent 110 that is generally formed at the 6 o'clock position. While, the vent 110 is shown as being a circular opening, the vent 110 can be formed to have any number of different shapes. The face mask 200 has an inner surface area of about 128 cm$^2$ and the vent 110 comprises an opening having an area of about 3.1 cm$^2$. Similar to the embodiment shown in FIG. 4, the face mask 200 also includes a pair of eye vents 220 formed on each side of the bridge section 210. The eye vents 220 are formed underneath the patient's eyes and can be formed to have any number of different shapes. Thus, the generally semicircular shape of the eye vents 220 is merely exemplary in nature and the eye vents 220 can have more of a rectangular shape according to another embodiment. The eye vents 220 function in the same manner as the eye vents described with reference to earlier embodiments in that they minimize the local velocity and particle inertia such that the particles do not impact on the surface of the face and eyes but rather actually pass over the face and eyes without deposition thereon. The eye vents 220 again serve to eliminate the interface between the face mask 200 and the face in the region of the eyes. According to one exemplary embodiment, the eye vents 220 are openings that occupy an area of about 3.4 cm$^2$.

Figure 12:
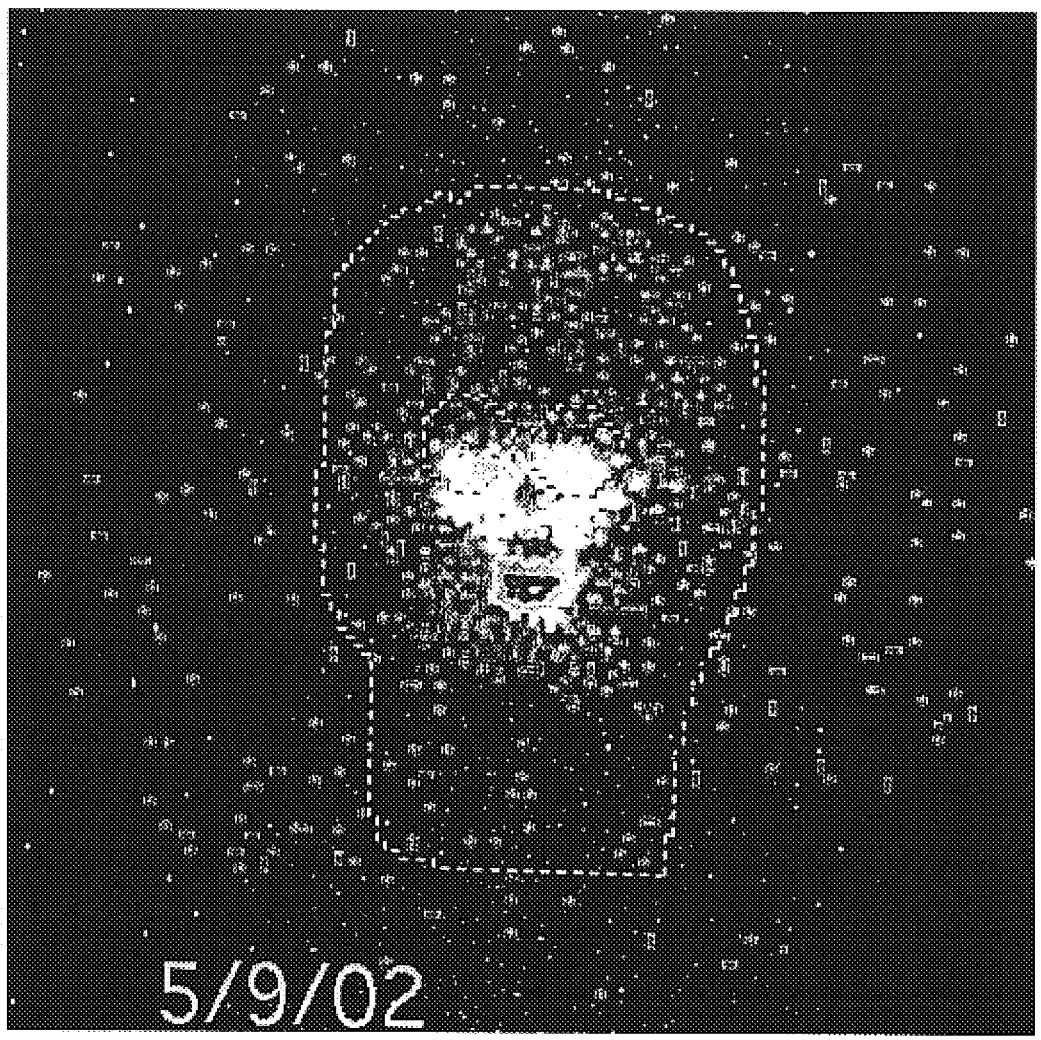
FIG. 12 is a an image obtained using a gamma camera scan of the face model as part of a radiolabel face deposition study carried out using the conventional face mask of FIG. 11 illustrating particle deposition (aerosol drug) occurring in response to a pediatric pattern of breathing (tidal volume 50 ml, frequency of breathing 25 breaths per min, duty cycle 0.4)

FIG. 12 is a gamma camera image obtained using a simulator face as part of radiolabel face deposition study carried out using the face mask 200 of FIG. 11 in combination with nebulizer 20. By using nebulized radiolabeled saline acting as a surrogate drug in the nebulizer, the deposition pattern of the particles is easily determined. FIG. 12 represents deposition following tidal breathing (tidal volume) of 50 ml with a minute ventilation of 1.25 liters/minute. Airflow from the nebulizer is 4.7 liters/minute and therefore the face mask 200 is highly pressurized. As can be seen from the image, the deposition of the aerosolized drug is not concentrated around the region of the eyes but rather the deposition is more spread out and less of the aerosolized drug is deposited onto the face itself. The benefits of the construction of face mask 200 will be further apparent in the discussion hereinafter of FIGS. 14 and 15.

Figure 13:
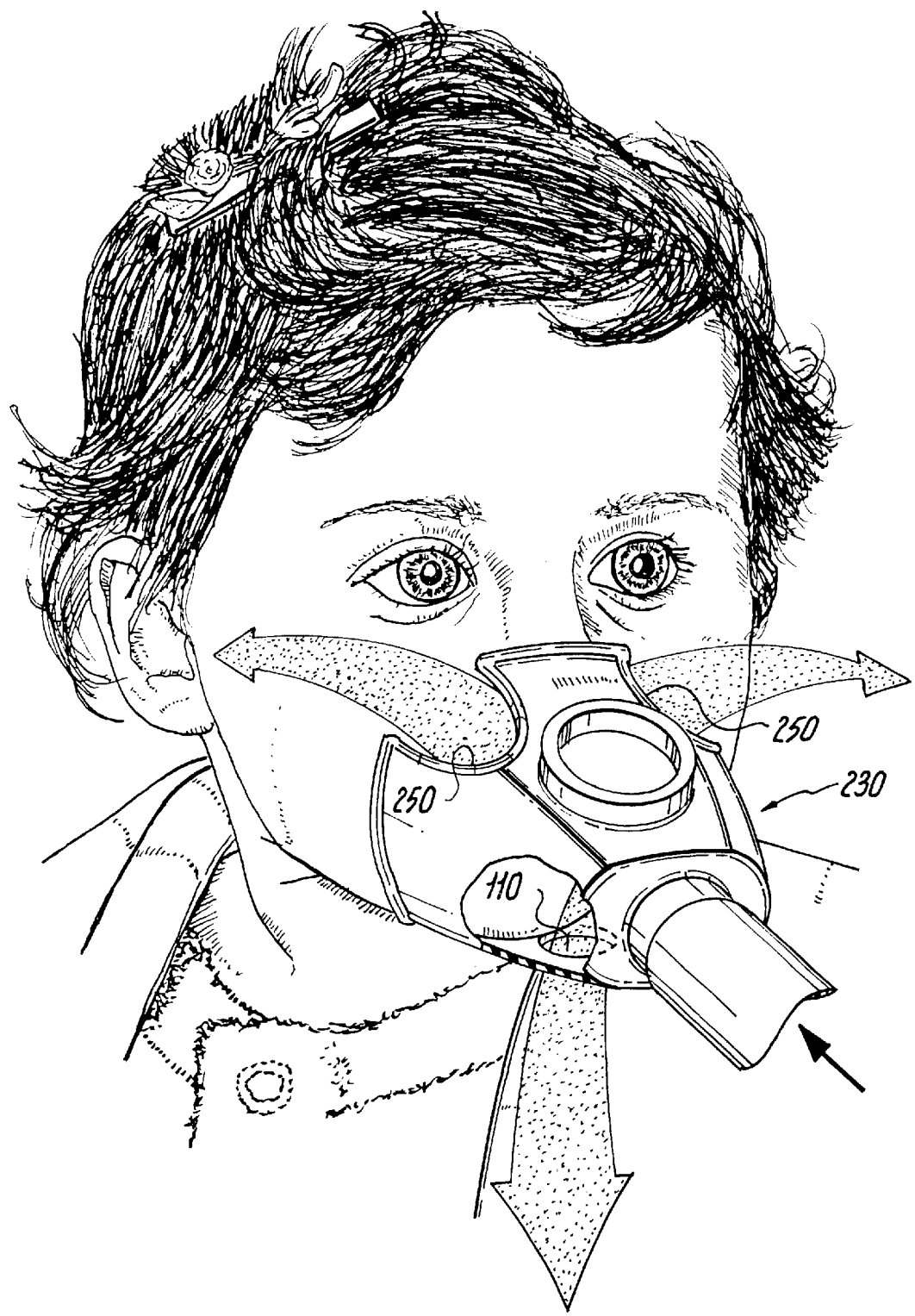
FIG. 13 is a front perspective view of a face mask according to a seventh exemplary embodiment shown as part of a nebulizer drug delivery system and in a typical administering position on a patient such that it is arranged so that the mask covers the nose and mouth of the patient, wherein the face mask has a pair of eye vents formed therein and wherein a portion of the face mask is cut away to illustrate a vent formed therein.

FIG. 13 illustrates a face mask 230 according to a sixth embodiment. The face mask 230 is very similar to the face mask 200 of FIG. 11 in that it is of the same general construction and it includes vent 110; however, the face mask 230 has larger eye vents 250 than the eye vents 220 of the face mask 200. The larger sized eye vents 250 are similar to the eye vents 150 illustrated in FIG. 5 and can also be reinforced, if necessary. According to one exemplary embodiment, the eye vents 250 comprise openings that occupy an area of about 9 cm$^2$. Each illustrated eye vent 250 has a semicircular shape; however, the shape of the eye vent 250 can vary. Accordingly, it will be appreciated that the area of eye vents that are formed in the face mask 200, 230 can vary depending upon a number of factors, including the acceptable robustness of the face mask, what type of modification of the flow characteristics is desired, etc. For example, the area that is occupied by the eye vents can be in the range from about 3.0 cm to about 10 cm$^2$. For this exemplary range, the eye vents occupy from about 2.3% to about 7.8% of the total surface area of the face mask.

It will be appreciated that the face masks 200, 230 are merely several examples of modifications to an existing face mask construction which is intended for use with a drug delivery system, such as a nebulizer drug delivery system, and there are a number of alternative type face masks that can be used and modified by forming eye vents therein either alone or in combination with one or more vents, such as a vent at the 6 o'clock position. It will therefore be understood that the face mask can be modified in the same manner as the face mask of any of the earlier embodiments (i.e., 6 o'clock vent alone, small eye vents alone, large eye vents alone, or a combination of the 6 o'clock vent with either the small or large eye vents).

Figure 14A:
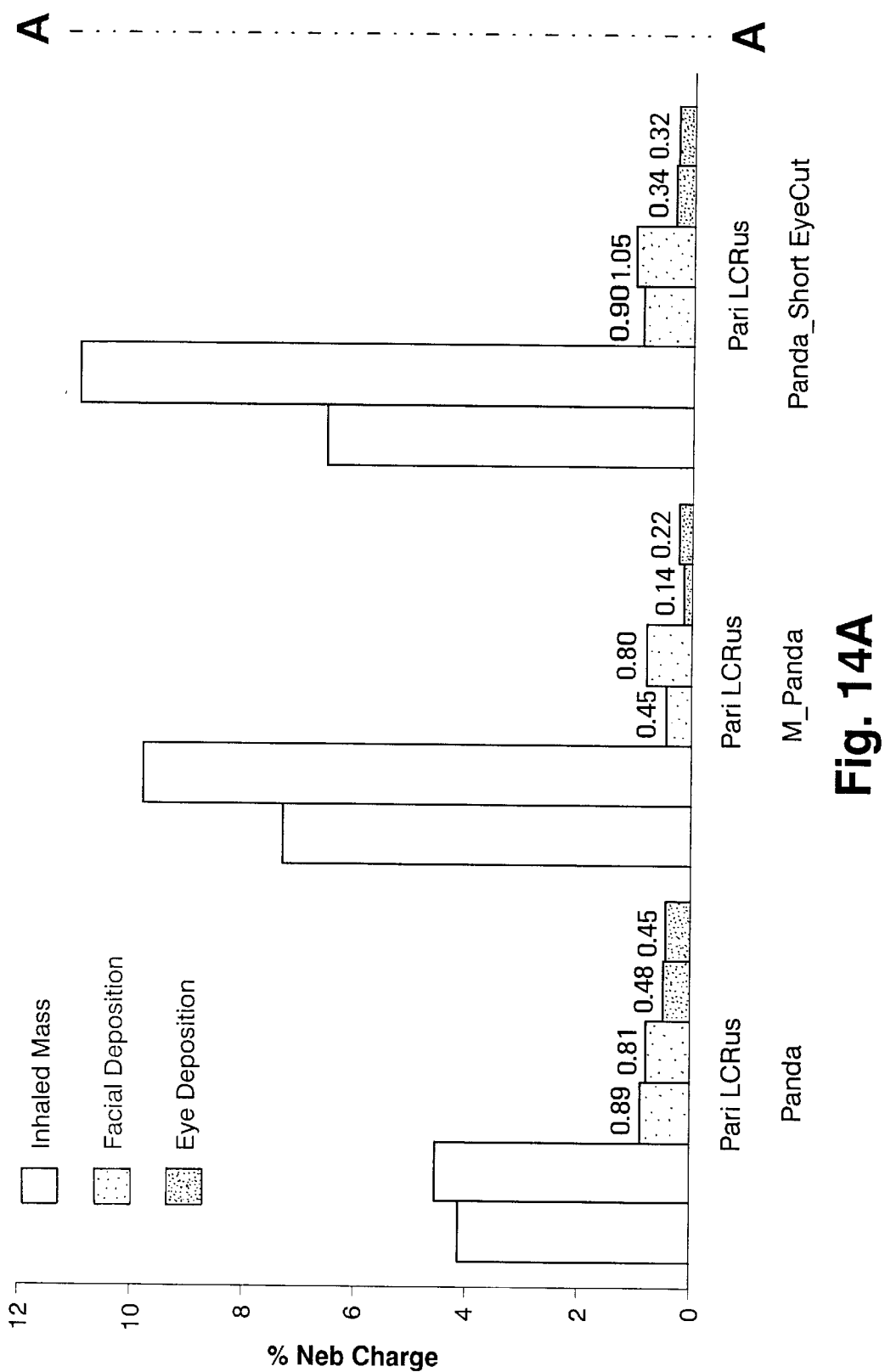
FIG. 14 is a schematic diagram in the form of a bar graph comparing drug delivery and facial deposition data obtained from testing a set of the exemplary face masks disclosed herein.
Figure 14B:
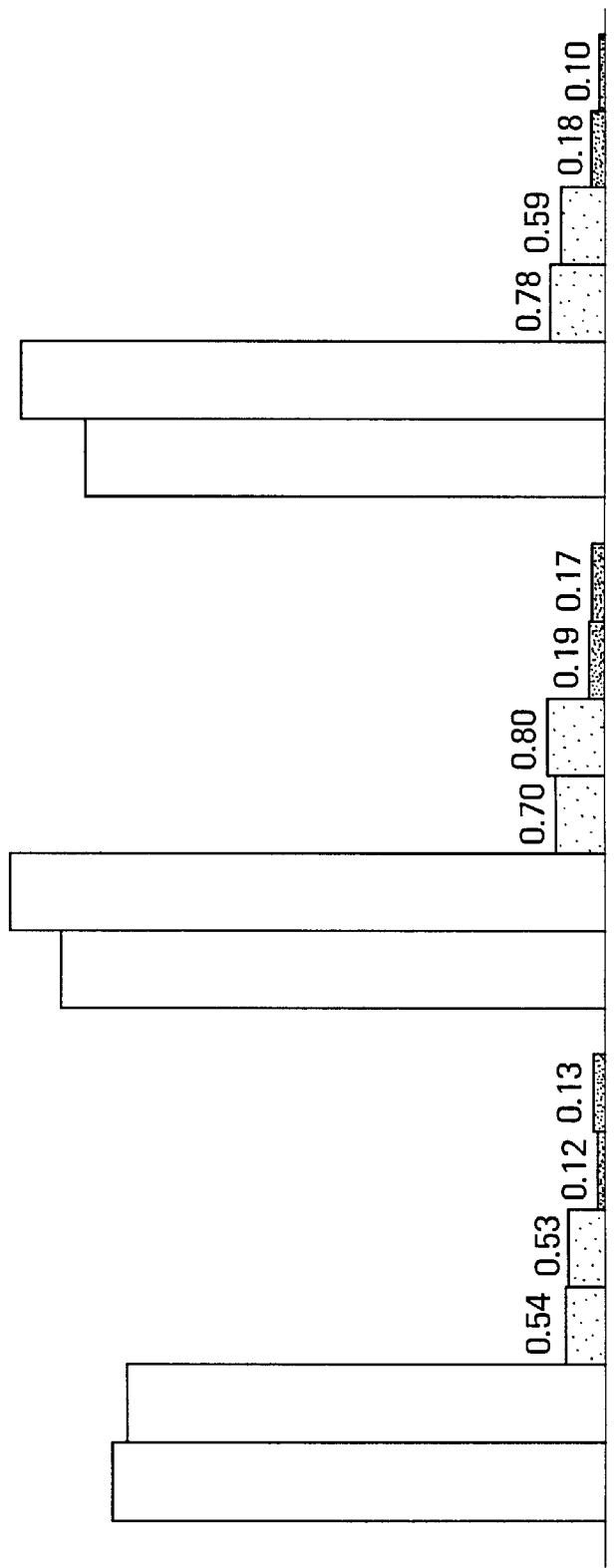

The bar graph of FIG. 14 and Table 2 of FIG. 15 summarize the quantitative measurements of deposition on the face, in the eyes and the drug delivery to the patient (inhaled mass). In FIGS. 14 and 15, a conventional face mask similar to the face mask 200 of FIG. 11 without vent 110 and vents 220 is identified as "Panda", a face mask similar to face mask 200 of FIG. 11 with only vent 110 is identified as "M Panda", a face mask similar to face mask 200 of FIG. 11 with only eye vents 220 is identified as "Panda ShortEyeCut", a face mask similar to face mask 240 of FIG. 13 with only the eye vents 250 is identified as "Panda LargeEyeCut", the face mask 200 of FIG. 11 is identified as "M Panda Short Eyecut", and the face mask 240 of FIG. 13 is identified as "M Panda Large Eyecut".

As the data of FIGS. 14 and 15 reflects, using a conventional face mask with a nebulizer resulted in 0.468% of the aerosolized drug initially placed in the nebulizer being deposited in the region of the eyes of the patient (0.846% of the aerosolized drug was deposited on the face). Thus, the amount of the aerosolized drug that was deposited in the eyes as a percentage of the amount deposited on the total face was 55.4%. In other words, more than half of the aerosolized drug that was deposited on the face was deposited in the area of highest risk, namely the eye regions. The inhaled mass (quantity of drug actually delivered to the patient) for the face mask was 4.499% of the amount placed in the nebulizer.

When the face mask was modified by forming only vent 110 therein, the inhaled mass increased to 8.66%, while at the same time, the amount of aerosolized drug being deposited in the region of the eyes decreased substantially to 0.18% (0.63% deposited on the face). Thus, only about 28.5% of the aerosolized drug that was deposited on the face was deposited in the region of the eyes. However, this data merely quantifies the results and does not characterize the flow properties of the aerosolized drug that does escape underneath the face mask and flows toward the eyes. In other words and as previously mentioned, the safety benefits accorded by the face mask are improved if not only less aerosolized drug is deposited in the region of the eyes (and on the face for that matter) but also if the flow characteristics of the escaping aerosolized drug are modified in the region of the eyes. The provision of eye vents in the face mask accomplishes these goals and enhances the overall safety of the face mask.

When only eye vents 220 are formed in the face mask, the inhaled mass increased to 8.85%, while at the same time, the amount of aerosolized drug being deposited in the region of the eyes was 0.33% (0.97% deposited on the face). When only eye vents 250 are formed in the face mask, the inhaled mass was 8.09% and the amount of aerosolized drug being deposited in the region of the eyes was 0.18% (0.75 deposited on the face).

The data for face mask 200 (vent 110 plus eye vents 220) reflects that the inhaled mass values is still within an acceptable range (6.92%), while the amount of aerosolized drug being deposited on the face was substantially reduced to 0.54% and further the amount deposited in the region of the eyes was reduced to 0.13%. This is a significant improvement over the standard face mask. When the face mask 240 was tested, the inhaled mass was 7.84% and the amount of aerosolized drug being deposited in the region of the eyes was 0.14% (with 0.69% being deposited on the face)

One other advantage of the forming eye vents in a face mask that is intended for use with a pressurized drug delivery system, such as a nebulizer, is that existing face masks can easily be retrofitted by simply forming the eye vents in the region of the eyes using conventional techniques, such as a cutting process or any other type of process that is capable of removing or excising the face mask material along distinct lines to form the eye vents.

The present applicant has recognized that certain drug delivery systems, particularly nebulizer drug delivery systems, enhance facial and eye exposure to aerosols. Nebulizer aerosol delivery utilizing face masks pressurizes the face mask and facilitates leaks at various points around the face mask with enhanced facial deposition. Maneuvers that reduce this pressurization reduce the leak and concomitant deposition. By incorporating eye vents into the face mask, the shortcomings of conventional face masks have been essentially eliminated. The eye vents act to reduce particle inertia in the region of the eyes Based on the data displayed on the images and quantified in Tables 1 and 2, the incorporation of eye vents can cause more than a 90% reduction in the amount of aerosolized drug that was deposited in the region of the eyes. It will be appreciated that the size and cross-sectional shape of the eye vents may be altered and optimized to minimize leak and maximize drug delivery. The size of the eye vents should be tailored so that the inhaled mass value is within acceptable ranges for the given application.

It will be understood that any of face masks disclosed herein can be used in any number of applications where the face mask is pressurized by a fluid to such a degree that pressurization in the face mask results in leaks being formed around the face mask. Preferably, the face mask is used in those applications where it is desirable to preserve inhaled mass values. In other words, the use of the face mask should allow a sufficient amount of the aerosolized drug to flow into the face mask reservoir and then subsequently into the respiratory system of the patient.

Eye vents can be incorporated into a vast number of medical face masks that are intended for use in drug delivery systems or the like. Furthermore, the use of any of the exemplary face masks is not limited to only aerosol drug delivery systems. It will be appreciated that the face mask can be used in other types of fluid delivery systems having the same or similar characteristics as the discussed aerosol drug delivery system, e.g., pressurization of the mask and leakage, etc. While a number of the illustrations and the experimental data are directed to use of the various face masks in pediatric applications, it will be understood that the face masks according to the present embodiments can be used in other applications besides pediatric applications. For example, the face masks can be worn by adults to administer an aerosolized drug, etc.

The foregoing written description is of a preferred embodiment and particular features of the present invention and is not restrictive of the many applications or the breadth of the present invention which is instead defined by the claims appended hereto and substantial equivalents thereof.

What is claimed is:

1. A face mask for use in a pressurized drug delivery system, the face mask comprising:

a body having a peripheral edge for placement against a face of a patient and a nose bridge section formed in an upper section of the body, the body having a pair of eye vents formed therein, with one eye vent being formed on one side of the nose bridge section and the other eye vent being formed the other side of the nose bridge section, the eye vents for placement underneath the eyes of the patient when the face mask is placed against the face of the patient, wherein each eye vent is at least partially open along the peripheral edge.

2. The face mask according to claim 1, wherein the face mask is coupled to a nebulizer drug delivery system for delivering an aerosolized drug through the face mask.

3. The face mask according to claim 1, wherein each eye vent comprises an eye cut out extending from the peripheral edge inwardly into the mask body.

4. The face mask according to claim 3, wherein one end of each eye cut defines an outer section of the nose bridge section.

5. The face mask according to claim 3, further including a reinforcing member disposed along a section of the peripheral edge that defines the eye cut out.

6. The face mask according to claim 5, wherein the reinforcing member comprises a stiffener formed of a rigid material that is attached to the mask body.

7. The face mask according to claim 5, wherein the reinforcing member comprises a section of the mask that is formed of a material that has a greater rigidity than mask material surrounding the reinforcing member.

8. The face mask according to claim 7, wherein the reinforcing member is formed of one of a reinforced plastic and a metal.

9. The face mask according to claim 1, wherein the eye vents occupy less than 10% of a total surface area of the face mask body.

10. The face mask according to claim 1, wherein the eye vents occupy between about 2% and about 10% of a total surface area of the face mask body.

11. A face mask for use in a pressurized drug delivery system, the face mask comprising:
a body having a peripheral edge for placement against a face of a patient and a nose bridge section formed in an upper section of the body, the body having a pair of eye vents formed therein, with one eye vent being formed on one side of the nose bridge section and the other eye vent being formed the other side of the nose bridge section, the eye vents for placement underneath the eyes of the patient when the face mask is placed against the face of the patient, wherein each of the pair of vents comprises an eye cut out which is formed along the peripheral edge of the face mask proximate to the nose bridge section.

12. The face mask according to claim 11, wherein the eye cut out has a substantially semicircular shape.

13. A face mask for use in a pressurized drug delivery system, the face mask comprising:
a body having a peripheral edge for placement against a face of a patient and a nose bridge section formed in an upper section of the body, the body having a pair of eye vents formed therein, with one eye vent being formed on one side of the nose bridge section and the other eye vent being formed the other side of the nose bridge section, the eye vents for placement underneath the eyes of the patient when the face mask is placed against the face of the patient, wherein each eye vent is defined by an arcuate edge that comprises a section of the peripheral edge of the mask body.

14. A face mask for use in a pressurized drug delivery system, the face mask comprising:
a body having a peripheral edge for placement against a face of a patient and a nose bridge section formed in an upper section of the body, the body having a pair of eye vents formed therein, with one eye vent being formed on one side of the nose bridge section and the other eye vent being formed the other side of the nose bridge section, the eye vents for placement underneath the eyes of the patient when the face mask is placed against the face of the patient, wherein the eye vents occupy greater than 10% of a total surface area of the face mask body.

15. A face mask for use in a pressurized drug delivery system, the face mask comprising:
a body having a peripheral edge for placement against a face of a patient and a nose bridge section formed in an upper section of the body, the body having a pair of eye vents formed therein, with one eye vent being formed on one side of the nose bridge section and the other eye vent being formed the other side of the nose bridge section, the eye vents for placement underneath the eyes of the patient when the face mask is placed against the face of the patient, wherein the eye vents are formed to have dimensions such that an inhaled mass of an aerosolized drug supplied through the face mask is greater than 4% of an initial amount of aerosolized drug that is present in the drug delivery system and an amount of the aerosolized drug that is deposited in a region of the eyes is less than 24% of an amount of the aerosolized drug that is deposited on the face under a pattern of breathing that is characterized as having a tidal volume of 50 ml, a frequency of breathing of 25 breaths per minute and a duty cycle of 0.4.

16. A face mask for use in a drug delivery system that delivers an aerosolized drug to a patient, the face mask comprising:
a body having a peripheral edge for placement against a face of the patient and a nose bridge section formed in an upper section of the body, the body having a pair of features formed therein on each side of the nose bridge section along a peripheral edge of the upper section of the body, the features being provided in perinasal sections of the mask that are prone to leakage of the aerosolized drug during administration of the aerosolized drug, wherein the features are constructed to reduce the particle inertia of any aerosolized drug that leaks through the perinasal sections and thereby reduce deposition of the aerosolized drug in eye regions of the patient.

17. The face mask of claim 16, wherein the pair of features comprises first and second eye vents that are each formed by cutting a section of the mask body along the peripheral edge in the upper section of the mask body on one side of the nose bridge section.

18. The face mask of claim 17, wherein each eye vent has a substantially arcuate edge defined by the cut peripheral edge of the body.

19. The face mask of claim 16, wherein the features are formed so as to reduce the local velocity of aerosolized drug that is vented in the perinasal sections around the nose bridge section by permitting the aerosolized drug to pass over and around eyes of the patient.

20. A method of reducing deposition of an aerosolized drug in eye regions of a patient wearing a face mask, the method comprising the step of:
altering flow characteristics of the aerosolized drug as it is vented through eye vents that are at least partially open along a peripheral edge of the face mask in perinasal areas thereof during application of the aerosolized drug.

21. The method of claim 20, wherein the step of altering the flow characteristics comprises reducing the local velocity of the aerosolized drug in the perinasal areas as the aerosolized drug is vented.

22. A method of reducing deposition of an aerosolized drug in eye regions of a patient wearing a face mask, the method comprising the steps of:
providing the face mask, the face mask having a body that includes a peripheral edge for placement against the face and a nose bridge section; and
forming a pair of eye vents in the body with one eye vent being formed on one side of the nose bridge section and the other eye vent being formed on the other side of the nose bridge section, the eye vents being formed in regions that normally experience fluid leaks with the eye vents being formed along and at least partially open at the peripheral edge in sections that are for placement underneath the eyes of the patient when the face mask is placed against the face, the eye vents reducing deposition in the eye regions by reducing the particle inertia of the aerosolized drug in the eye regions.

23. The method of claim 22, wherein forming each eye vent comprises the step of:

cutting a section of the body along the peripheral edge to form an eye cut out.

24. The method of claim 22, further including the step of:

forming a supplemental vent in the mask body.

25. The method of claim 24, wherein the supplemental vent comprises an opening formed in mask body opposite the nose bridge section.

26. A face mask for use in a pressurized drug delivery system, the face mask comprising:

a body having a peripheral edge for placement against a face of a patient and a nose bridge section formed in an upper section of the body, the body having a pair of vents formed therein in perinasal sections of the mask that are prone to leakage, with one vent being formed in the upper section on one side of the nose bridge section and the other vent being formed in the upper section on the other side of the nose bridge section, the two vents at least partially defining the nose bridge section, the vents for placement underneath the eyes of the patient when the face mask is placed against the face of the patient.

* * * * *